United States Patent [19]

Le Fur et al.

[11] Patent Number: 4,956,173

[45] Date of Patent: Sep. 11, 1990

[54] COMPOSITION AND USE OF ADEMETIONINE AGAINST AGEING OF THE SKIN

[75] Inventors: Gérard Le Fur, Montmorency; Michéle Bousquet, Bievres, both of France; Emilio Crisafulli, Milan, Italy; Michel Sabadie, Bernay, France

[73] Assignee: Societe Anonyme: SANOFI, Paris, France

[21] Appl. No.: 275,834

[22] Filed: Nov. 25, 1988

[30] Foreign Application Priority Data

Nov. 25, 1987 [FR] France ................... 87 16349

[51] Int. Cl.$^5$ .................. A61K 7/48; A61K 31/70
[52] U.S. Cl. ............................ 424/63; 514/46
[58] Field of Search .............. 536/26; 424/63; 514/46

[56] References Cited

U.S. PATENT DOCUMENTS

| | | | |
|---|---|---|---|
| 4,057,686 | 11/1977 | Fiecchi | 536/26 |
| 4,465,672 | 8/1984 | Gennari | 514/46 |
| 4,543,408 | 9/1985 | Gennari | 536/26 |
| 4,764,603 | 8/1988 | Zappia | 536/26 |

FOREIGN PATENT DOCUMENTS

| | | |
|---|---|---|
| 1218986 | 3/1987 | Canada . |
| 0108817 | 5/1984 | European Pat. Off. . |
| 0148057 | 7/1985 | European Pat. Off. . |
| 2275220 | 2/1976 | France . |
| 3389 | 4/1989 | PCT Int'l Appl. . |

*Primary Examiner*—Merrell C. Cashion, Jr.
*Assistant Examiner*—Susan S. Rucker
*Attorney, Agent, or Firm*—Foley & Lardner, Schwartz, Jeffery, Schwaab, Mack, Blumenthal & Evans

[57] ABSTRACT

The present invention relates to the use of ademetionine or one of its salts for the preparation of pharmaceutical or cosmetic compositions for counteracting ageing of the skin.

It further relates to the said cosmetic compositions.

21 Claims, No Drawings

COMPOSITION AND USE OF ADEMETIONINE AGAINST AGEING OF THE SKIN

The present invention relates to the use of ademetionine and its salts for the preparation of cosmetic and pharmaceutical compositions for counteracting ageing of the skin, and to the cosmetic compositions thus obtained.

Ademetionine is the International Common Name of the inner salt of (S)-5'-[(3-amino-3-carboxypropyl)methylsulfonio]-5'-deoxyadenosine hydroxide of the formula

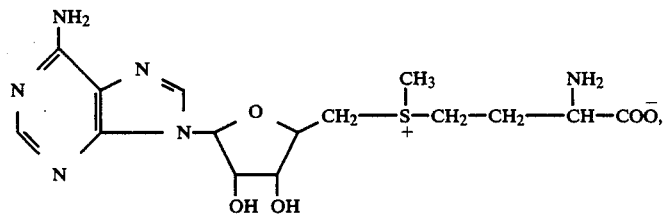

which is also called S-adenosyl-L-methionine or, more simply, SAM.

Ademetionine is a physiological molecule of virtually ubiquitous distribution in the tissues and in the liquids of the organism, where it is involved in important biological processes as a donor of methyl groups in numerous transmethylation reactions and as a precursor of physiological sulfur compounds such as glutathione, cysteine, taurine and CoA.

The levels of ademetionine are known to be high in children and adolescents, whereas they are lower in adults and subsequently decrease in presenility and senility.

Ademetionine is the active principle of drugs used especially for the treatment of degenerative osteoarthropathy, where it has an important role through its antiphlogistic and analgesic activity due to its intervention in the metabolism of arachidonic acid and prostaglandins without interfering with platelet aggregation.

Ademetionine is also indicated in the treatment of depressive syndromes.

This active principle is neither toxic nor mutagenic and the drugs in which it is present have no troublesome side-effects. These drugs are administered intramuscularly, intravenously or orally, although the possibility of administering them topically in liquids and ointments, in which the active principle is diluted in ordinary solvents used in pharmacy, has been mentioned (U.S. Pat. No. 4,057,686).

Ademetionine in the form of the inner salt is unstable and it is preferably used, in pharmaceutical compositions, in the form of salts with inorganic and/or organic acids such as carboxylic acids, for example as the citrate, tartrate, malate or ascorbate (French patent No. 2 275 220), with strong mineral acids having a pK of less than 2.5 (European patent No. 73 376) and with organic sulfonic acids having a pK of less than 2.5 (European patent No. 72 980, Belgian patent No. 831,310), the preferred salt being the sulfate p-toluenesulfonate or the disulfate di-p-toluenesulfonate. Salts with polyanions have also been proposed (European patent No. 191 133). To guarantee the good stability of preparations based on ademetionine, however, it is desirable to mix the active principle with a stabilizer, for example mannitol (European patent No. 73 376), lactose or maltose (European patent No. 108 817).

Ademetionine has now been found to counteract ageing of the skin.

More particularly, it has been found that ademetionine, dissolved or dispersed in a suitable vehicle, delays ageing of the skin by also giving it a pleasant appearance and a pleasant firmness.

Thus, according to one of its aspects, the present invention relates to the use of ademetionine and its salts for the preparation of pharmaceutical or cosmetic compositions for counteracting ageing of the skin.

It relates more precisely to a method of treating the skin—to counteract ageing—which consists in using ademetionine or one of its salts in association with a cosmetically or pharmaceutically acceptable vehicle.

The anti-ageing action is due to the biochemical properties of ademetionine. Transmethylation has been shown to take place on biological molecules, especially skin proteins, nucleic acids and phospholipids, which are biotransformed and enter anabolic and catabolic cycles. This anabolic-catabolic activity on the epidermal cells favors their regeneration, while the action on the methyltransferases, by increasing the methylation of the phospholipids, makes the cell membranes more fluid and thereby slows down the natural skin ageing process.

This membrane-fluidizing action has been demonstrated on human epidermal cells. The membrane microviscosity of human epidermal cells has been studied by the method of Shnitzkym et al. (J. Biol. Chem. 1974, 249, 2652–2657) using diphenylhexatriene as a fluorescent marker. The presence of ademetionine at a molar concentration of $10^{-6}$ to $10^{-4}$ reduces the membrane viscosity by 10 to 25%.

According to the present invention, ademetionine can be used in the form of any one of the salts indicated above, preferably the dihydrochloride, the disulfate, the salt with 2.5 molecules of sulfuric acid, the p-toluenesulfonate, the di-p-toluenesulfonate, the tri-p-toluenesulfonate or the disulfate di-p-toluenesulfonate, or salts with polyanions. Among the latter, the salts with a cellulose sulfate, such as the cellulose 6-sulfate described in European patent No. 116 251, with a chitin sulfate, such as the chitin 6-sulfate described in European patent No. 116 251, or with a chitosan sulfate, such as the chitosan 6-sulfate described in European patent No. 148 057, are particularly preferred.

The ademetionine salts can be used as such or in the presence of stabilizers, for example mannitol, lactose or maltose, and/or adjuvants such as a fatty acid.

Mannitol is generally present in a ratio ademetionine or one of its salts/mannitol of about 3/1.

For the preparation of the pharmaceutical or cosmetic compositions according to the invention, the ademetionine and its salts are used in sufficient amounts to produce the therapeutic or cosmetic effect, especially at a concentration of 0.001 to 5% by weight; a desirable concentration is 0.001 to 1% and preferably 0.05 to 0.2%.

The active principle is mixed with pharmaceutical or cosmetic excipients in order to prepare salves, creams, lotions, emulsions or solutions.

The active principle can also be converted to a form suitable for oral or parenteral administration, by known processes.

To prepare pharmaceutical compositions for local use, the active principle is mixed with the excipients generally employed in the art of pharmacy for compositions for topical use, such as, for example, fats of animal origin, vegetable oils, saturated or unsaturated fatty acids, alcohols, polyalkylene glycols, waxes, petroleum jelly and polyesters, which can be used in association with water and gelling agents if they are compatible. Other ingredients compatible with ademetionine and its salts, such as antibacterial agents or fragrances, can be added to these preparations.

The ademetionine, especially in the form of one of its salts, is preferably used for the preparation of cosmetic compositions for counteracting ageing of the skin, and more particularly for:

slowing down ageing by maintaining an optimum fluidity of the membranes of the skin cells, a high membrane fluidity favoring internal intercellular exchanges and hence an optimum metabolism; and improving the condition of skin aged prematurely by the action of exogenous factors, according to the above process.

The ademetionine salt is used as such or in the form of an encapsulation complex, for example of the liposome or phytosome type, coated with a protective film or complexed with a protein system, in order to prepare cosmetics in the form of emulsions, aqueous or anhydrous gels, two-phase systems to be mixed immediately before use, in which the ademetionine salt is in solid form, make-up products, or lotions which may or may not be based on alcohol, if appropriate in the presence of a stabilizer.

According to another aspect, the present invention therefore relates to cosmetic compositions based on ademetionine or one of its salts. In these compositions, the ademetionine is preferably used in the form of a salt, preferably one of the salts mentioned above, and, if appropriate, mixed with a stabilizer such as mannitol, lactose, maltose or a cyclodextrin, the preferred stabilizer being mannitol.

When an ademetionine salt/stabilizer mixture is used, the preferred mixture is ademetionine disulfate di-p-toluenesulfonate/mannitol in a ratio of 2:1 to 4:1, preferably 3:1.

The cosmetic compositions of the present invention can also contain adjuvants such as saturated or unsaturated fatty acids containing from 1 to 18 carbon atoms, which may or may not be substituted by a hydroxyl group, or an alkali metal salt of the said fatty acids.

In these compositions, the concentration can be 0.001 to 5%; the desirable concentration is 0.001 to 1%, preferably 0.05 to 0.2% by weight.

The cosmetic compositions according to the invention can be in the form of a cream in which the ademetionine, one of its salts or a mixture of one of these products with the stabilizer is associated with the excipients which are commonly used in cosmetology and which are compatible with ademetionine and its salts, such as lanolin.

The cosmetic compositions of the invention can also be in the form of a gel in suitable excipients such as cellulose esters, fatty acid esters, for example isopropyl myristate, or other gelling agents.

The cosmetic compositions according to the invention can also take the form of a lotion or solution in which the ademetionine, its salt or a mixture of one of these products with the stabilizer is dissolved or microdispersed in a microemulsion.

The pharmaceutical or cosmetic compositions according to the invention can therefore be in the form of a microdispersion of ademetionine in a liquid containing water together with one or more surfactants. These dispersions have the properties of microemulsions and in practice have the appearance of true solutions. They are preferably prepared immediately before use.

These microemulsions possess a good stability and can be kept for the necessary time for use at temperatures of between 0° and 60° C. without sedimentation of the constituents or phase separation.

The surfactants of the composition are selected from the surface-active agents which can be used in cosmetology. The following may be indicated by way of non-limiting examples: sorbitol esters and their polyethoxylated derivatives, polyethoxylated castor oils (hydrogenated or non-hydrogenated), ethylene oxide/propylene oxide block copolymers, polyethoxylated fatty alcohols, sodium laurylsulfate, sodium dioctylsulfosuccinate and egg or soya lecithins.

If the ademetionine is used in the form of a salt, the pH can be kept in the region of neutrality, if desired, by adding a neutralizing agent to the composition. The neutralizing agent, if added, can consist either of a buffer mixture, for example a phosphate buffer, or simply of a biocompatible amine such as mono-, di- or tri-ethanolamine.

In a preferred embodiment, the use of surfactants with a Hydrophilic Lipophilic Balance (HLB) of between 10 and 17 and preferably of between 11 and 15, in an amount of 7 to 40%, gives microemulsions which can be diluted in water in all proportions, irrespective of the hardness of the water used.

Such dilutions remain stable for several days, which is very adequate in view of their use.

The pharmaceutical or cosmetic compositions of the present invention are very well tolerated, they have no phototoxicity and their application to the skin for prolonged periods of time does not give rise to any systemic effects. In general, after thirty days of application, there is a noticeable improvement in the appearance of the skin and a noticeable slowing-down of wrinkle formation.

The Examples which follow illustrate the invention without however implying a limitation. The following abbreviations will be used in these Examples:

SAM=ademetionine
SAM-2s,2t=ademetionine disulfate di-p-toluenesulfonate
SAM-2s=ademetionine disulfate For the sake of simplification, certain constituents of the compositions have been denoted by their tradenames, which have the following meanings:
Aerosil 200: silica aerosol, marketed by DEGUSSA
Solutol HS 15: polyethylene glycol 600 12-hydroxystearate, marketed by BASF
Labrafil 1944 CS: polyethoxylated unsaturated fatty acid triglycerides, marketed by GATTEFOSSE Acrysol: acrylate/methacrylate copolymer, marketed by SEPPIC
Finsolv TN: benzoates of alcohols containing 12-15 carbon atoms, marketed by WITCO
Cetiol HE: polyethylene glycol-7 glyceryl cocoate, marketed by HENKEL
Labrafac hydrophile: polyethoxylated triglycerides containing 7-8 carbon atoms, marketed by GATTEFOSSE
Abil 8551 B: dimethicone copolyol, marketed by GOLDSCHMIDT
Carbopol 934: carboxypolymethylene, marketed by GOLDSCHMIDT
Carbopol 940: carboxypolymethylene, marketed by GOLDSCHMIDT
EDTA: ethylenediaminetetraacetic acid
UVA-UVB filter: 2-ethylhexyl 4-methoxycinnamate (trademark PARSOL MCX).

EXAMPLE 1

Gel based on a 3/1 SAM disulfate ditosylate/mannitol mixture, containing 1% of SAM base

| SAM-2s,2t | 2.88 g |
|---|---|
| Aerosil 200 | 7.00 g |
| Isopropyl myristate ad | 100.00 g |

EXAMPLE 2

Microemulsion to be prepared immediately before use

| SAM-2s,2t | 0.1% |
|---|---|
| Solutol HS 15 | 2.0% |
| Labrafil 1944 CS | 1.0% |
| Water qs | 100.0% |

The microemulsion is prepared by mixing all the excipients and stirring until a clear solution is obtained. The component SAM-2s,2t is added at the time of use and the resulting microemulsion remains stable for several days.

EXAMPLE 3

Microemulsion to be prepared immediately before use, obtained as described in Example 2

| SAM-2s,2t | 0.1% |
|---|---|
| Solutol HS 15 | 4.0% |
| Labrafil 1944 CS | 2.0% |
| Water qs | 100.0% |

EXAMPLE 4

Microemulsion to be prepared immediately before use, obtained as described in Example 2

| SAM-2s,2t | 0.1% |
|---|---|
| Finsolv TN | 5.5% |
| Solutol HS 15 | 8.0% |
| Water qs | 100.0% |

EXAMPLE 5

Microemulsion to be prepared immediately before use, obtained as described in Example 2

| SAM-2s,2t | 0.1% |
|---|---|
| Solutol HS 15 | 4.0% |
| Labrafil 1944 CS | 2.0% |
| Hydroxyethyl cellulose | 0.5% |
| Water qs | 100.0% |

EXAMPLE 6

Microemulsion to be prepared immediately before use, obtained as described in Example 2

| SAM-2s,2t | 0.1% |
|---|---|
| Solutol HS 15 | 4.0% |
| Labrafil 1944 CS | 2.0% |
| Hydroxyethyl cellulose | 1.0% |
| Water qs | 100.0% |

EXAMPLE 7

Microemulsion to be prepared immediately before use, obtained as described in Example 2

| SAM-2s,2t | 0.1% |
|---|---|
| Solutol HS 15 | 4.0% |
| Labrafil 1944 CS | 2.0% |
| Acrysol | 1.0% |
| Water qs | 100.0% |

EXAMPLE 8

Microemulsion to be prepared immediately before use, obtained as described in Example 2

| SAM-2s,2t | 0.1% |
|---|---|
| Solutol HS 15 | 4.0% |
| Labrafil 1944 CS | 2.0% |
| Acrysol | 2.0% |
| Water qs | 100.0% |

EXAMPLE 9

Microemulsion to be prepared immediately before use, obtained as described in Example 2

| SAM-2s,2t | 0.10% |
|---|---|
| Solutol HS 15 | 1.00% |
| Labrafac hydrophile | 0.25% |
| Cetiol HE | 0.20% |
| Abil 8551 B | 0.05% |
| Propylene glycol | 12.50% |
| Ethanol | 12.50% |
| Carbopol 934 | 0.40% |
| Triethanolamine qs | pH 6 |
| Fragrance qs | |
| Colorant qs | |
| Water qs | 100.0% |

EXAMPLE 10

Preparation for immediate use

| A/Solvent: | |
|---|---|
| Carboxymethyl cellulose | 0.30 g |
| Preservatives in propylene glycol: | 5.00 g |
| Phenoxyethanol | 0.5 g |
| Methyl 4-hydroxybenzoate | 0.1 g |
| Ethyl 4-hydroxybenzoate | 0.1 g |

| -continued | |
|---|---|
| Propyl 4-hydroxybenzoate | 0.1 g |
| Butyl 4-hydroxybenzoate | 0.1 g |
| Propylene glycol | 4.1 g |
| Ethoxylated hydrogenated castor oil | 1.00 g |
| Fragrance | 0.20 g |
| Demineralized water qs | 100.00 g |
| B/Powder: | |
| SAM-2s | 0.01 g |
| Lactose qs | 100.00 g |

EXAMPLE 11

| Night cream | |
|---|---|
| Cetyl alcohol | 2.00 g |
| Stearin | 2.50 g |
| Glycerol monostearate | 5.00 g |
| Isopropyl palmitate | 5.00 g |
| Vegetable oil | 3.00 g |
| Mineral oil | 2.00 g |
| Perhydrosqualene | 2.00 g |
| Silicone oil | 1.00 g |
| Shea butter | 2.00 g |
| 2-Ethylhexyl palmitate | 5.00 g |
| Triethanolamine | 5.50 g |
| Preservatives in butylene glycol: | 5.00 g |
| Phenoxyethanol | 0.5 g |
| Methyl 4-hydroxybenzoate | 0.1 g |
| Ethyl 4-hydroxybenzoate | 0.1 g |
| Propyl 4-hydroxybenzoate | 0.1 g |
| Butyl 4-hydroxybenzoate | 0.1 g |
| Butylene glycol | 4.1 g |
| Tetrasodium EDTA | 0.10 g |
| Fragrance | 0.30 g |
| SAM-2s | 0.01 g |
| Water qs | 100.00 g |

EXAMPLE 12

| Protective day cream | |
|---|---|
| Ethoxylated sorbitan monostearate | 2.60 g |
| Silicone oil | 1.00 g |
| Cetyl alcohol | 2.00 g |
| Mineral oil | 3.00 g |
| Lanolin alcohol | 1.00 g |
| Perhydrosqualene | 1.00 g |
| Sorbitan monostearate | 2.40 g |
| Cetyl palmitate | 3.00 g |
| Isopropyl palmitate | 4.00 g |
| UVA-UVB filter | 2.00 g |
| Tetrasodium EDTA | 0.10 g |
| Carbopol | 0.30 g |
| Triethanolamine | 0.30 g |
| Alpha-tocopherol | 0.01 g |
| Preservatives in butylene glycol: | 5.00 g |
| Phenoxyethanol | 0.5 g |
| Methyl 4-hydroxybenzoate | 0.1 g |
| Ethyl 4-hydroxybenzoate | 0.1 g |
| Propyl 4-hydroxybenzoate | 0.1 g |
| Butyl 4-hydroxybenzoate | 0.1 g |
| Butylene glycol | 4.1 g |
| Fragrance | 0.30 g |
| SAM-2s | 0.01 g |
| Demineralized water qs | 100.00 g |

EXAMPLE 13

| Gel | |
|---|---|
| Carbopol 940 | 0.20 g |
| Polyethylene glycol | 3.00 g |
| Alpha-tocopherol | 0.01 g |
| Preservatives in butylene glycol: | 5.00 g |

| -continued | |
|---|---|
| Gel | |
| Phenoxyethanol | 0.5 g |
| Methyl 4-hydroxybenzoate | 0.1 g |
| Ethyl 4-hydroxybenzoate | 0.1 g |
| Propyl 4-hydroxybenzoate | 0.1 g |
| Butyl 4-hydroxybenzoate | 0.1 g |
| Butylene glycol | 4.1 g |
| Fragrance | 0.30 g |
| Triethanolamine | 0.25 g |
| SAM-2s | 0.01 g |
| Demineralized water qs | 100.00 g |

EXAMPLE 14

| Fluid make-up foundation | |
|---|---|
| Ethoxylated soya sterols | 4.00 g |
| Soya sterols | 0.50 g |
| Glycerol monostearate | 1.00 g |
| Vegetable oil | 1.50 g |
| 2-Ethylhexyl palmitate | 4.00 g |
| Cetyl alcohol | 0.50 g |
| Capric/caprylic triglycerides | 1.50 g |
| Silicone oil | 1.00 g |
| Mineral oil | 1.80 g |
| Lanolin alcohol | 0.20 g |
| Propylene glycol dipelargonate | 3.00 g |
| Lecithin | 1.00 g |
| Preservatives in butylene glycol: | 5.00 g |
| Phenoxyethanolamine | 0.5 g |
| Methyl 4-hydroxybenzoate | 0.1 g |
| Ethyl 4-hydroxybenzoate | 0.1 g |
| Propyl 4-hydroxybenzoate | 0.1 g |
| Butyl 4-hydroxybenzoate | 0.1 g |
| Butylene glycol | 4.1 g |
| Carbopol | 0.20 g |
| Triethanolamine | 0.20 g |
| Tetrasodium EDTA | 0.10 g |
| Alpha-tocopherol | 0.01 g |
| Fragrance | 0.30 g |
| SAM-2s | 0.01 g |
| Demineralized water qs | 100.00 g |

What is claimed is:

1. A method of treating the skin of a living human to counteract aging, which comprises applying to the skin a cosmetic or pharmaceutical preparation containing an effective amount of ademetionine or a salt thereof dissolved or dispersed in a cosmetically or pharmaceutically acceptable vehicle for topical administration.

2. The method of claim 1, wherein a salt of ademetionine is used, said salt being ademetionine disulfate di-p-toluenesulfonate or ademetionine disulfate.

3. The method of claim 1, wherein a salt of ademetionine is used, said salt being a salt of ademetionine with a polyanion.

4. The method of claim 3, wherein the said polyanion is selected from a cellulose sulfate, a chitin sulfate or chitosan 6-sulfate.

5. The method of claim 1, wherein said ademetionine or salt thereof is present in combination with a stabilizer selected from the group consisting of mannitol, lactose and maltose.

6. The method of claim 5, wherein said stabilizer is mannitol, and wherein the ratio of ademetionine or ademetionine salt to mannitol is about 3 to 1.

7. The method of claim 1, wherein said ademetionine or a salt thereof is applied in the form of a microemulsion prepared immediately before use.

8. The method of claim 1, wherein said ademetionine or a salt thereof is applied at a concentration in said vehicle of between 0.001 and 5% by weight.

9. The method of claim 8, wherein the concentration of said ademetionine or a salt thereof is between 0.001 and 1% by weight in said vehicle.

10. The method of claim 8, wherein the concentration of said ademetionine or a salt thereof is between 0.05 and 0.2% by weight in said vehicle.

11. A cosmetic composition, which comprises ademetionine or a salt thereof, dissolved or dispersed in a cosmetically acceptable vehicle for topical administration, said ademetionine or salt being contained in said composition in an amount sufficient to counteract ageing of the skin by maintaining fluidity of the membranes of the skin cells.

12. The cosmetic composition of claim 11, which further comprises a stabilizer.

13. The cosmetic composition of claim 12, wherein said ademetionine or salt thereof is ademetionine disulfate di-p-toluenesulfonate, said stabilizer is mannitol, and the ratio of said ademetionine disulfate di-p-toluenesulfonate to said mannitol is about 3 to 1.

14. The composition of claim 11, wherein said ademetionine or salt thereof is ademetionine disulfate.

15. The composition of claim 11, wherein said ademetionine or a salt thereof is present in a concentration of 0.001 to 5% by weight in said cosmetically acceptable vehicle.

16. The cosmetic composition of claim 15, wherein said ademetionine or a salt thereof is present in said vehicle in a concentration of 0.001 to 1% by weight.

17. The method of claim 7, wherein said microemulsion further comprises a surfactant in an amount of 7 to 40%, said surfactant having a hydrophilic lipophilic balance of between 10 and 17.

18. The method of claim 17, wherein said surfactant has a hydrophilic lipophilic balance of between 11 and 15.

19. The cosmetic composition of claim 11, which further comprises an unsubstituted saturated or unsaturated fatty acid containing 1 to 18 carbons, a hydroxy saturated or unsaturated fatty acid containing 1 to 18 carbons, or an alkali metal salt thereof.

20. The cosmetic composition of claim 12, wherein said ademetionine or a salt thereof is ademetionine disulfate.

21. The cosmetic composition of claim 16, wherein said ademetionine or a salt thereof is present in said vehicle in a concentration of 0.05 to 0.2% by weight.

* * * * *